(12) United States Patent
Kirsch et al.

(10) Patent No.: US 6,503,225 B1
(45) Date of Patent: Jan. 7, 2003

(54) DEVICE FOR REMOVAL OF GAS BUBBLES AND DISSOLVED GASSES IN LIQUID

(75) Inventors: Claudia F. E. Kirsch, New York, NY (US); Bradley W. Reed, Gastonia, NC (US)

(73) Assignee: Celgard Inc., Charlotte, NC (US)

( * ) Notice: Subject to any disclaimer, the term of this patent is extended or adjusted under 35 U.S.C. 154(b) by 0 days.

(21) Appl. No.: 09/530,309
(22) PCT Filed: Aug. 26, 1998
(86) PCT No.: PCT/US98/17718
§ 371 (c)(1), (2), (4) Date: Oct. 23, 2000
(87) PCT Pub. No.: WO99/32186
PCT Pub. Date: Jul. 1, 1999

Related U.S. Application Data

(63) Continuation of application No. 09/111,143, filed on Jul. 7, 1998, now abandoned.
(60) Provisional application No. 60/077,892, filed on Mar. 13, 1998, and provisional application No. 60/068,426, filed on Dec. 22, 1997.

(51) Int. Cl.$^7$ .............................................. A61M 1/00
(52) U.S. Cl. ................................. 604/126; 422/48
(58) Field of Search ................................ 604/118, 126; 96/8; 210/321.8, 645, 137; 422/48

(56) References Cited

U.S. PATENT DOCUMENTS

| | | | | |
|---|---|---|---|---|
| 4,219,422 A | * | 8/1980 | Knothe et al. | 210/137 |
| 4,571,244 A | * | 2/1986 | Knighton | 604/118 |
| 4,909,989 A | * | 3/1990 | Fukazawa et al. | 422/48 |
| 5,034,125 A | * | 7/1991 | Karbachsch et al. | 210/321.8 |
| 5,288,308 A | * | 2/1994 | Puri et al. | 96/8 |
| 6,086,770 A | * | 7/2000 | Malkovich | 210/645 |
| 6,267,926 B1 | * | 7/2001 | Bradley et al. | 422/48 |

* cited by examiner

Primary Examiner—Teresa Wallberg
Assistant Examiner—Leonid M Fastovsky
(74) Attorney, Agent, or Firm—Robert H. Hammer, III

(57) ABSTRACT

A device (10) for removal of gas bubbles and dissolves gasses from fluids delivered into a patient during medical procedures is disclosed. A housing (20) having a number of gas permeable hollow fibers (50) passing therethrough is provided. The infused fluid is introduced through the interior lumens of the hollow fibers (50), and entrained or dissolved gasses are drawn through the fiber walls to the outer or shell side of the fibers. A vacuum may be drawn on the housing through a vent (32) to enhance gas removal. A passage (70) is optionally provided through the device to allow a tool or other device to be passed therethrough.

27 Claims, 2 Drawing Sheets

DEVICE FOR REMOVAL OF GAS BUBBLES AND DISSOLVED GASSES IN LIQUID

CROSS-REFERENCE TO RELATED APPLICATIONS

This application is a continuation of Ser. No. 09/111,143 filed Jul. 7, 1998 now abandoned which claims the benefit of prior filed copending U.S. Provisional Patent Application Serial No. 60/077,892, filed Mar. 13, 1998, and of prior filed copending U.S. Provisional Patent Application Serial No. 60/068,426, filed Dec. 22, 1997. The contents of U.S. Provisional Patent Application Serial Nos. 60/077,892 and 60/068,426 are hereby incorporated herein by reference.

BACKGROUND OF THE INVENTION

1. Field of the Invention

The present invention relates generally to the medical field; and more particularly to a device for removal of gasses from fluids delivered to a patient during a medical procedure.

2. Description of Related Art

It is often desirable to introduce one or more fluids to an internal site of a patient during a medical procedure. The fluid introduced can be, for example, a drug, an anesthetic, blood, saline, flush solution, a marker dye, intravenous nutrients, or other bioactive fluids or soluble medications. Fluid delivery may be necessary or desirable in medical procedures including conventional angiography, interventional angiography, neurointerventional angiography, cardiac catheterization, arterial pressure monitoring, Swanz-Ganz catheterization, indwelling catheters, and intravenous or interarterial delivery procedures.

In order to prevent or minimize the risk of injury to the patient from air embolism, it is generally necessary to eliminate air or other gasses from the fluid delivered. Typically, fluid delivery lines are manually cleared of visible air bubbles by flushing prior to use. Existing drip chamber devices used with some fluid delivery systems to reduce the likelihood of air embolism must be maintained in an upright position to prevent the formation of air bubbles in a fluid delivery line. Thus, inadvertent tilting of the device can endanger the patient. The risk of air bubble formation increases with increasing drip rate. Dissolved gasses within the delivered fluid can form bubbles out of solution due to pressure changes, temperature changes, flow irregularities, or other factors. Thus it can be seen that a need yet exists for a gas elimination device for removing gas bubbles and/or dissolved gas from fluids delivered to an internal site of a patient during a medical procedure. A further need exists for such a device that is not required to be maintained in an upright configuration, and that permits use with standard fluid delivery equipment. A need also exists for such a device that can be located at a point in the fluid delivery line near the patient, to minimize the potential for bubble formation between the device and the patient.

It is frequently desirable to access the internal site of delivery of the fluid, as by a surgical tool, and/or monitoring equipment. previously known devices typically do not make provision for access therethrough. Thus, it can be seen that a need exists for a gas elimination device that permits access to the fluid delivery site by a surgical tool or monitoring device.

It is to the provision of a gas elimination device meeting these and other needs that the present invention is primarily directed.

SUMMARY OF THE INVENTION

Briefly described, in preferred form, one aspect of the invention is a device for removing gas bubbles and dissolved gases from fluids introduced to a patient during medical procedures. The device can be used for intravenous or intraarterial applications, including without limitation: conventional angiography, interventional angiography, neurointerventional angiography, cardiac catheterization, arterial pressure monitoring, Swanz-Ganz catheters, syringes or intravenous lines for injection of drugs or solutes or nutrients, arterial lines, venous lines, and indwelling catheters, or during operative procedures. The device preferably includes a housing having a first end comprising an inlet port, a second end comprising an outlet port, an interior surface extending between the inlet port and the outlet port, and a vent port between the inlet port and the outlet port. The device preferably further includes at least one hollow fiber membrane within the housing, each having a first end adjacent the inlet port and a second end adjacent the outlet port. A first fluid tight seal is provided between the first end of the at least one hollow fiber membrane and the interior surface of the housing. A second fluid tight seal is provided between the second end of the at least one hollow fiber membrane and the interior surface of the housing.

In another aspect, the present invention comprises a device for removal of gas from a liquid, the device comprising a housing having a fluid inlet, a fluid outlet and a gas vent; a sealed chamber within the housing between the fluid inlet and the fluid outlet, and in communication with the gas vent; and a plurality of hollow fiber membranes extending through the sealed chamber, each having a first end in communication with the fluid inlet and a second end in communication with the fluid outlet.

In another aspect, the present invention comprises a device for removal of gas from a liquid infused to an internal delivery site, and for allowing passage of a medical implement to the internal delivery site. The medical implement may be, for example, a catheter, a catheter guide wire, a probe, a laparoscope, or another surgical or monitoring instrument. The device preferably includes a housing comprising a fluid inlet, a fluid outlet and a gas vent. A sealed chamber is preferably provided within the housing between the fluid inlet and the fluid outlet. The sealed chamber is in communication with the gas vent. A plurality of hollow fiber membranes extend through the sealed chamber, each having a first end in communication with the fluid inlet and a second end in communication with the fluid outlet. A passage is provided through the sealed chamber for allowing passage of the medical implement through the device to the delivery site. The passage comprises a first end in communication with the fluid inlet, a second end in communication with the fluid outlet, and a sleeve extending between the first and second ends.

Another aspect of the present invention is a method of removing gas from a liquid infused to an internal delivery site of an organism, and accessing the internal delivery site with a medical implement. The method preferably includes passing the liquid through at least one hollow fiber membrane within a housing; degassing the liquid by removing gasses through pores in the at least one hollow fiber membrane; infusing the liquid to the internal delivery site; and accessing the internal delivery site by passing the medical implement through a passage extending through the housing.

Another aspect of the present invention is a method of fabricating a device for removal of a gas from a liquid. The method preferably comprises providing a housing having an inlet port, an outlet port and a vent port; installing a plurality of hollow fiber membranes within the housing, extending generally from adjacent the inlet port to adjacent the outlet port; installing an annulus within the housing, extending generally from adjacent the inlet port to adjacent the outlet port; and applying first and second sealing means at the ends of the plurality of hollow fiber membranes and the ends of the annulus, to form a fluid tight seal between the plurality of hollow fiber membranes, the annulus, and the housing.

These and other features and advantages of preferred forms of the present invention are described more fully herein with reference to the accompanying drawing figures.

BRIEF DESCRIPTION OF THE DRAWING FIGURES

DETAILED DESCRIPTION

Figure 1:
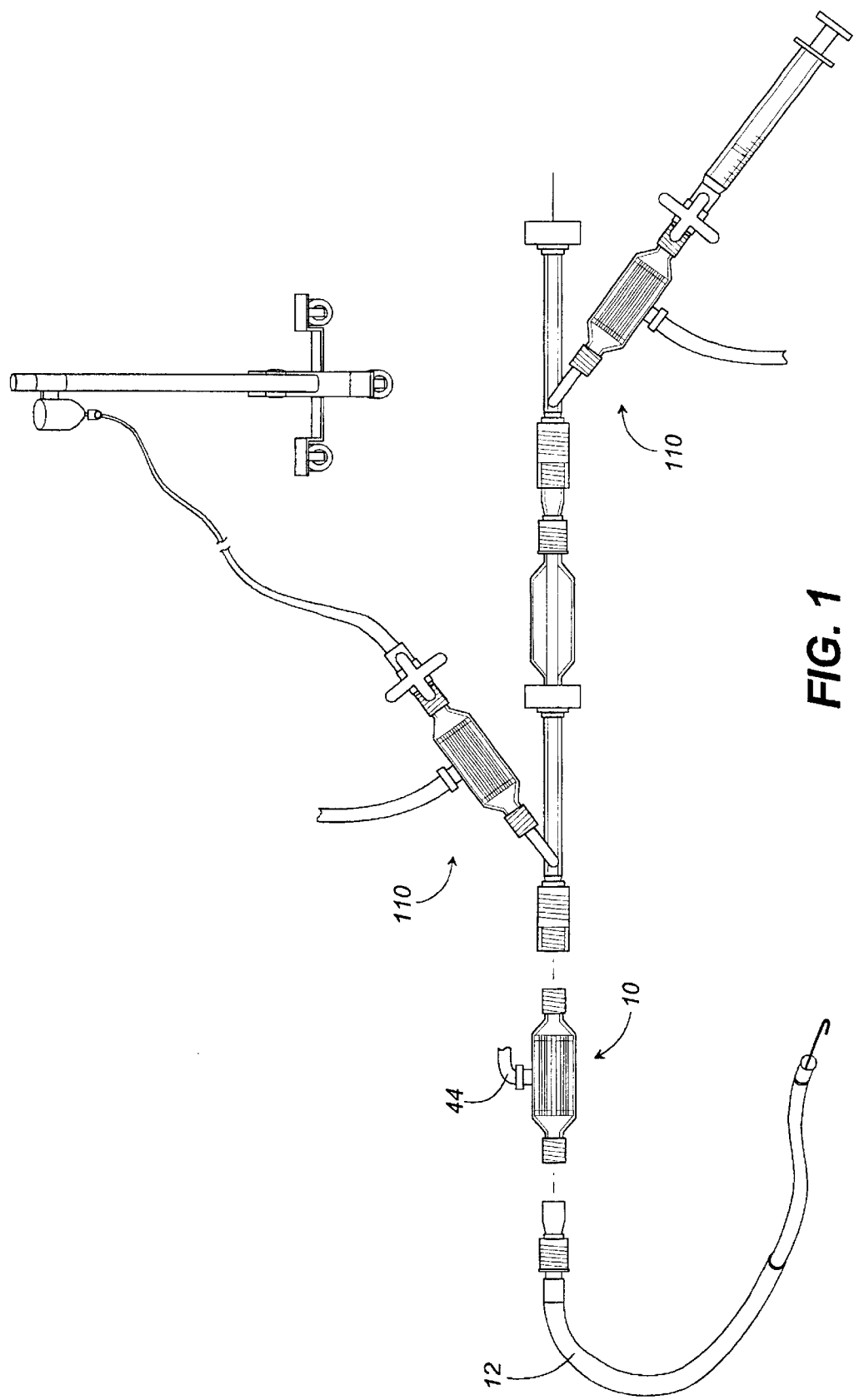
FIG. 1 shows preferred forms of the device of the present invention in situ in a catheter infusion system.
Figure 5:
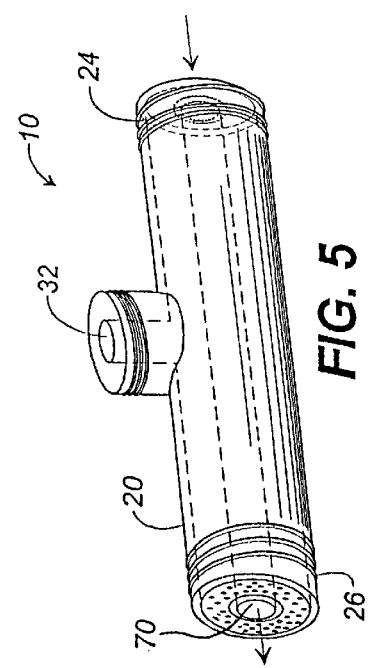
FIG. 5 shows a perspective view of another form of the device of the present invention.
Figure 2:
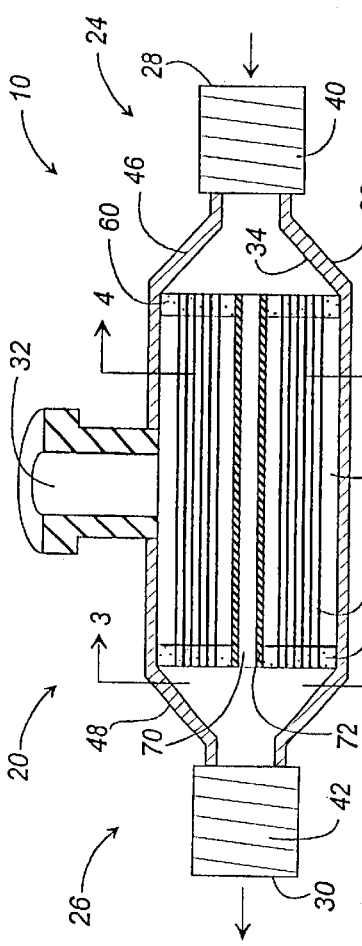
FIG. 2 shows a side view, in partial cross-section, of one form of the device of the present invention.
Figure 4:
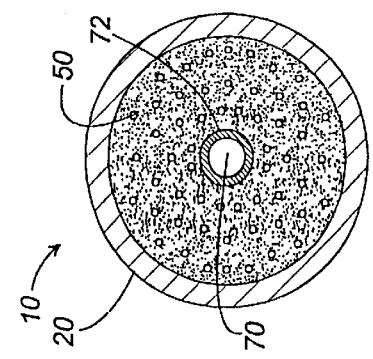
FIG. 4 shows a cross-sectional view of the device shown in FIG. 2, taken along line 4—4.
Figure 3:
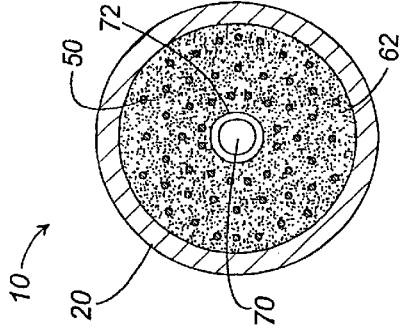
FIG. 3 shows a cross-sectional view of the device shown in FIG. 2, taken along line 3—3.

FIGS. 2–4 show a device 10, according to one preferred embodiment of the present invention. The device 10 can be coupled to any fluid infusion line, such as the catheter flush line 12 as shown in FIG. 1, for removal of gas bubbles and dissolved gas from the fluid passing through the line. The device 10 includes a fluid-tight housing 20, which is preferably fabricated from a rigid FDA grade material, such as polycarbonate, as a "T" or "Y" fitting. The housing 20 generally comprises a body portion 22, and first and second ends 24, 26. First end 24 comprises an inlet port 28 for receiving a liquid, and second end 26 comprises an outlet port 30 for discharging the degassed liquid for delivery to an internal delivery site of a patient. A vacuum or vent port 32 is also provided in the housing between the inlet 28 and the outlet 30. The housing 20 further comprises an interior surface 34 and an exterior surface 36 extending between first and second ends 24, 26. First and second endcaps 40, 42 can be provided at first and second ends 24, 26 of the housing, and can be provided with detachable couplings for coupling the device 10 to the line 12. The endcaps 40, 42 can be integrally formed with the body portion 22 of the housing 20, as by injection molding or other known fabrication methods; or can be separately formed and attached to the body portion 22 by solvent welding, ultrasonic welding, thermal welding, adhesives, or other attachment means. The detachable couplings can comprise threaded, compression, twist-lock, or other fittings. In a preferred embodiment, Luer lock quick-connect fittings are provided at the first and second ends of the housing 20. The vacuum or vent port 32 can also be provided with a quick-connect fitting, threads or other detachable coupling means for connection to an external vacuum source through a vacuum line 44 (FIG. 1). The housing 20 can take any of a number of physical configurations, including the cylindrical housing with reduced diameter neck portions 46, 48 at its first and second ends 24, 26 shown in FIGS. 1 and 2, and the straight-walled cylinder configuration shown in FIG. 5. The housing 20 can be a commercially-available "T" or "Y" fitting, or can be specially fabricated for the particular application involved. In the alternate design shown in FIG. 5, the housing is formed as a single cylindrical piece, with generally straight walls having detachable couplings formed at each end thereof.

At least one, and preferably a plurality of hollow fiber membranes 50 extend generally axially through the housing 20, from adjacent the first end 24 to adjacent the second end 26. Each fiber extends between a first end adjacent the inlet 28 and a second end adjacent the outlet 30. The fibers 50 can be a microporous hydrophobic hollow fiber membrane, such as are available commercially as polyolefin membranes. Example materials include: polypropylene, polyethylene, or polymethylpentene. The fibers 50 typically have an outside diameter of approximately 200–400 microns, a wall thickness of approximately 25–50 microns, a pore size of between approximately 0.01 to 0.2 microns (sufficiently small to prevent fluid breakthrough), and a porosity of approximately 10–50% (sufficiently high to provide adequate flux of gas and gas bubble passage from the aqueous fluid in the internal lumens of the fibers 50 to the gas phase exterior of the fibers 50). The fiber membranes 50 are constructed of suitable FDA grade materials. A porous hydrophobic membrane allows for direct removal of bubbles from aqueous fluids without liquid penetration into the pores according to the Young-Laplace formula. Removal of dissolved gasses present in the liquid can be additionally facilitated by use of vacuum on the shell side of the device, through the vacuum or vent port 32, due to partial pressure difference of the gasses in the liquid and gas phases according to Henry's Law.

Although microporous hydrophobic hollow fiber membranes are described above, any porous hollow fiber material, whether hydrophobic or hydrophilic, can be used to form the fibers 50, with the application of a thin coating or skin of a polymer having suitable permeability to the dissolved gasses (for example, oxygen, nitrogen, carbon dioxide) in the aqueous fluid passed through the tubing 12, but rendering the pores of the fibers 50 impermeable to passage of the aqueous fluid therethrough. Example polymer coatings include silicones, polymethylpentene, and other FDA grade polymers. The polymer skin is preferably applied to the liquid surface (the internal lumen surface) of the hollow fiber 50, to prevent liquid penetration into the pores. Vacuum applied to the shell side of the device 10 through the vent 32 facilitates removal of dissolved gasses from the liquid. Although the polymer skin typically prevents direct removal of bubbles present in the liquid, entrained bubbles in the liquid will dissolve into the liquid once sufficient dissolved gasses are removed from the liquid. Once dissolved, the gasses can be removed from the liquid.

The fiber membranes 50 are held in place at their first and second ends within the housing 20 by first and second fluid tight seals 60, 62. The first and second seals 60, 62 can comprise, for example, a potting resin that fills the voids between the fibers 50, and bonds to the interior surface 34 of the housing 20 to form a fluid tight seal once hardened or cured. The potting resin can comprise, for example, a multicomponent (resin and hardener component) thermosetting or UV-curable FDA grade resin, such as for example, silicone, urethane or epoxy, all of which will provide secure attachment of the fibers 50 within the housing 20, as well as insuring a fluid tight seal around the fibers 50 and against the interior surface 34. As seen best in the cross-sectional view of FIG. 3, the fluid tight seals 60, 62 (seal 62 is depicted in FIG. 3) are closely formed around the external surfaces of the fibers 50 and, if present, the sleeve 72, which is more fully described below. As seen best in the cross-sectional view of FIG. 4, the fibers 50 and, if present, the sleeve 72 extend freely between the first and second fluid tight seals 60, 62. Alternatively, intermediate supports and/or baffles can be provided between the first and second fluid tight seals 60, 62. The first and second fluid tight seals 60, 62, along with the interior surface 34 of the housing 20, define a sealed chamber 66 within the housing 20. The sealed chamber 66 is in communication with the vent 32, thereby allowing gasses within the chamber 66 to be exhausted, and allowing a vacuum to be applied to the chamber 66 through the vent 32. As seen best in FIG. 2, the sealed chamber 66 is arranged between the inlet 28 and the outlet 30, and the hollow fiber membranes 50 extend through the chamber 66. The first ends of the fibers 50 are in communication with the fluid inlet 28, and the second ends of the fibers 50 are in communication with the fluid outlet 30. In this manner, any fluids transferred from the inlet 28 to the outlet 30 must pass through the interior lumens of the fibers 50.

In its more preferred forms, the invention further comprises one or more passages 70, extending through the sealed chamber 66, and having first and second ends extending through the first and second fluid tight seals 60, 62. The passage 70 allows an implement such as a surgical tool or instrument to pass through the device 10 and access the internal site of fluid delivery. For ease of access, the first end of the passage 70 is preferably generally aligned with and in communication with the inlet 28, and the second end of the passage 70 is generally aligned with and in communication with the outlet 30. Although one passage 70 is depicted, multiple passages may be provided. For example one passage may be provided for access by a surgical tool, and another passage may be provided for access by a monitoring device such as a fiberoptic endoscope. The passage 70 preferably comprises a generally tubular sleeve 72 extending generally axially through the center of the interior of the housing 20. Each end of the sleeve 72 is held in place, and a fluid tight seal is formed around the exterior surfaces thereof, by the first and second fluid tight seals 60, 62. The sleeve 72 is preferably constructed of a suitable FDA grade polymeric material such as polycarbonate, polypropylene or polyethylene. Tool sealing means can be provided, for example, by selecting the inner diameter of the sleeve 72 to generally match the outer diameter of the tool or device intended to be inserted therethrough, so as to slidingly engage the tool and form a seal against fluid passage through the passage 70 between the sleeve 72 and the tool. Alternatively, the tool sealing means can comprise a separate tool-sealing element, such as a flexible rubber or plastic lip, gasket or O-ring provided in the passage 70. Although the passage 70 has been described as tubular, it may have a cross-sectional geometry other than circular, as required to match the outer geometry of the tool or device to be passed therethrough. Closure means can also be provided for maintaining the passage 70 closed to fluid passage when the tool is not installed therethrough. The closure means and the tool sealing means can comprise the same or different components. For example, the sleeve 72 can be formed from a resilient, flexible material, which will stretch to permit passage of the tool or device and automatically create a sealing engagement with the outer surface thereof, regardless of its shape, and contract to close the passage 70 when the tool is not installed therethrough. Alternatively, a flap, iris, spring mechanism, elastic band, or other closure means, biased to closure against fluid passage but openable upon insertion of a tool or other device, can be provided within the passage 70 or adjacent the sleeve 72.

Figure 6:
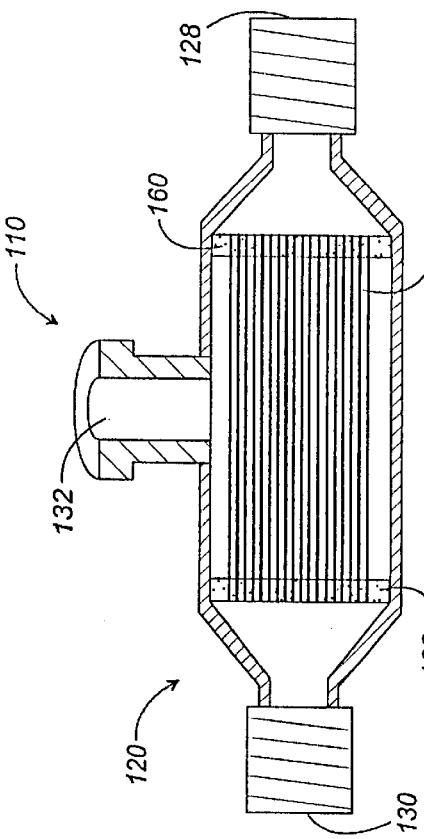
FIG. 6 shows a side view, in partial cross-section, of another form of the device of the present invention.

FIG. 6 shows another preferred form of the present invention. This embodiment of the device 110 can be generally similar to the devices described herein with reference to FIGS. 2–5, with the exception of the absence of the tubular sleeve 72 that forms the passage 70. As shown in FIG. 1, the device 110 can be used in sections of the fluid delivery system wherein passage of a tool or other device is not required, for example, for gas removal from a fluid line between an intravenous drip bag or a syringe and the flush line 12. The device 110 preferably includes a housing 120, an inlet 128, an outlet 130, and a vent 132. A plurality of hollow fiber membranes 150 preferably extend between first and second fluid tight seals 160, 162. Fluid is passed from the inlet 128 to the outlet 130 through the hollow fiber membranes 150, and bubbles and/or dissolved gasses are removed from the fluid through the hollow fiber membranes 150 and discharged through the vent 132. If desired, a vacuum can be applied to the vent 132 to enhance gas removal.

Methods of fabrication and use of the device of the present invention will now be described. Although these methods are described with reference to the embodiment of the device 10 depicted by FIGS. 2–5, it will be understood that other embodiments, such as for example the device 110 depicted by FIG. 6, can be fabricated and used according to similar methods, with the omission of the sleeve 72 and the passage of a tool or other device through the passage 70. The device 10 can be fabricated by inserting the hollow fibers 50 and the sleeve 72 through the housing 20, extending from adjacent the inlet port 28 to adjacent the outlet port 30. The fibers 50 and the sleeve 72 preferably initially extend somewhat beyond the housing ends, and/or are sealed at their ends to prevent ingress of potting resin into the interior lumens thereof during construction. The first and second fluid tight seals 60, 62 are then formed around the fibers 50 and the sleeve 72 by applying a seal forming material such as potting resin across the interior surface 34 of the housing 20 adjacent the first and second ends 24, 26. The seal forming material fills the spaces between the fibers 50 and the sleeve 72, and bonds to the interior surface 34 of the housing 20, thereby forming the fluid-tight seals and isolating the sealed chamber 66 from the inlet 28 and the outlet 30. The potting resin is cured or allowed to harden. The ends of the fibers 50 and the sleeve 72 are cut approximately flush with the outer surfaces of the first and second fluid tight seals 60, 62, thereby exposing the open ends of the lumens of the fibers 50 and the sleeve 72.

The device 10 of the present invention is utilized by installing the device 10 in a fluid infusion line, such as the catheter flush line 12 as shown in FIG. 1. The outlet port 30 of the housing 20 is connected, preferably by means of quick connect fittings, to an end of the catheter line 12. The inlet port 28 of the housing 20 is connected to an infusion and access system, which may include one or more fluid delivery means such as the two depicted syringe and flush solution line arrangements, and one or more access points such as the depicted guide wire insertion point. In many applications, it will be desirable to install the device as close to the fluid delivery site as possible, in order to minimize the potential for bubble formation between the device and the fluid delivery site. An external vacuum source may be connected to the vacuum port 32 of the housing 20, through the vacuum line 44, to apply a negative relative pressure to the shell side of the device 10 to assist in drawing gasses out of the liquid through the walls of the fibers 50. Fluids may then be infused from the fluid delivery means, through the lumens of the fibers 50, and through the infusion line 12. As the fluids pass through the lumens of the fibers 50, gas bubbles and/or dissolved gasses in the fluids are removed from the fluids through the pores of the fibers 50, and out the vent or vacuum port 32 in the housing 20. Because liquids do not pass through the pores in the fibers 50, the gas-stripped liquid continues through the lumens of the fibers 50. A tool or other device, such as the depicted catheter guide wire, can be inserted into the guide wire insertion point, passed through the passage 70, and through the catheter line 12. The outer geometry of the device preferably fits in close engagement with the inner diameter of the sleeve 72 to act as a seal against fluid passage. In addition to the depicted guide wire, a variety of devices may be inserted through the system as described. For example, a fiberoptic endoscope may be inserted to view internal tissue, and/or surgical instruments may be inserted to carry out any of a number of surgical procedures.

While the invention has been described in its preferred forms, it will be readily apparent to those of ordinary skill in the art that many additions, modifications and deletions can be made thereto without departing from the spirit and scope of the invention.

What is claimed is:

1. A device for removal of gas from a liquid in a medical fluid infusion line, said device comprising:
    (a) a housing having a first end comprising an inlet port, a second end comprising an outlet port, an interior surface extending between said inlet port and said outlet port, and a vacuum port between said inlet port and said outlet port;
    (b) a plurality of hollow fiber membranes within said housing, each said hollow fiber membrane having a first end adjacent the inlet port and a second end adjacent the outlet port;
    (c) a first fluid tight seal between the first end of each said hollow fiber membrane and the interior surface of the housing; and
    (d) a second fluid tight seal between the second end of each said hollow fiber membrane and the interior surface of the housing.

2. The device of claim 1, wherein each said hollow fiber membrane comprises a microporous hydrophobic material.

3. The device of claim 2, wherein said microporous hydrophobic material comprises a polyolefin.

4. The device of claim 3, wherein said polyolefin comprises polypropylene.

5. The device of claim 3, wherein said polyolefin comprises polyethylene.

6. The device of claim 3, wherein said polyolefin comprises polymethylpentene.

7. The device of claim 1, wherein each said hollow fiber membrane comprises a hollow fiber microtubing with a gas permeable coating.

8. The device of claim 7, wherein said gas permeable coating comprises silicon.

9. The device of claim 7, wherein said gas permeable coating comprises polymethylpentene.

10. The device of claim 7, wherein said gas permeable coating is applied to an internal lumen of said hollow fiber microtubing.

11. The device of claim 1, wherein each said hollow fiber membrane comprises a material having a porosity of approximately 10–50%.

12. The device of claim 11, wherein said material comprises a plurality of pores having a pore size of approximately 0.01 to 0.2 microns.

13. The device of claim 1, wherein said first and second fluid tight seals comprise a potting resin selected from the group consisting of thermosetting resins, UV-curable resins, silicone, urethane and epoxy.

14. The device of claim 1, wherein said inlet port and said outlet port comprise detachable couplings for releasably engaging fluid delivery conduit.

15. The device of claim 1, wherein said vacuum port comprises a detachable coupling for releasably engaging a vacuum line.

16. The device of claim 1, further comprising a sealed passage extending through said first and second fluid tight seals.

17. The device of claim 16, wherein said sealed passage comprises a sleeve having a first end generally aligned with said inlet port of said housing and a second end generally aligned with said outlet port of said housing.

18. The device of claim 17, further comprising tool sealing means for slidably engaging a tool received in said sleeve.

19. The device of claim 16, further comprising closure means for maintaining said sealed passage closed to fluid passage.

20. The device of claim 16, wherein said sealed passage comprises a resilient flexible material.

21. A device for removal of gas from a liquid in a medical fluid infusion line, said device comprising:
    (a) a housing comprising a fluid inlet, a fluid outlet and a vacuum vent;
    (b) a sealed chamber within said housing between said fluid inlet and said fluid outlet, said sealed chamber being in communication with said vacuum vent; and
    (c) a plurality of hollow fiber membranes extending through said sealed chamber, each of said plurality of hollow fiber membranes having a first end in communication with said fluid inlet and a second end in communication with said fluid outlet.

22. The device of claim 21, wherein said plurality of hollow fiber membranes comprise a microporous hydrophobic material.

23. The device of claim 21, wherein said plurality of hollow fiber membranes comprise porous hollow fiber microtubes having a gas permeable coating.

24. The device of claim 21, wherein said housing comprises a first endcap adjacent said fluid inlet, and a second endcap adjacent said fluid outlet, and wherein said first and second endcaps and said vacuum vent comprise detachable couplings.

25. The device of claim 21, further comprising a passage through said sealed chamber, said passage comprising a first end in communication with said fluid inlet, a second end in communication with said fluid outlet, and a sleeve extending between said first and second ends.

26. A device for removal of gas from a liquid infused to an internal delivery site, and for allowing passage of a medical implement to the internal delivery site, said device comprising:

(a) a housing comprising a fluid inlet, a fluid outlet and a vacuum vent;

(b) a sealed chamber within said housing between said fluid inlet and said fluid outlet, said sealed chamber being in communication with said vacuum vent;

(c) a plurality of hollow fiber membranes extending through said sealed chamber, each of said plurality of hollow fiber membranes having a first end in communication with said fluid inlet and a second end in communication with said fluid outlet; and (d) a passage through said sealed chamber, said passage comprising a first end in communication with said fluid inlet, a second end in communication with said fluid outlet, and a sleeve extending between said first and second ends.

27. A method of removing gas from a liquid infused to an internal delivery site of an organism, and accessing the internal delivery site with a medical implement, the method comprising:

(a) passing the liquid through at least one hollow fiber membrane within a housing;

(b) degassing the liquid by removing gasses through pores in the at least one hollow fiber membrane;

(c) infusing the liquid to the internal delivery site; and (d) accessing the internal delivery site by passing the medical implement through a passage extending through the housing.

* * * * *